US011723621B2

(12) United States Patent
Keidar

(10) Patent No.: US 11,723,621 B2
(45) Date of Patent: *Aug. 15, 2023

(54) HEART VALVE MONITORING

(71) Applicant: Edwards Lifesciences Corporation, Irvine, CA (US)

(72) Inventor: Yaron Keidar, Kiryat Ono (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 16/986,730

(22) Filed: Aug. 6, 2020

(65) Prior Publication Data

US 2021/0169444 A1 Jun. 10, 2021

Related U.S. Application Data

(63) Continuation of application No. 16/171,501, filed on Oct. 26, 2018, now Pat. No. 10,835,201.

(Continued)

(51) Int. Cl.
*A61B 5/02* (2006.01)
*A61B 8/06* (2006.01)
(Continued)

(52) U.S. Cl.
CPC ............ *A61B 8/065* (2013.01); *A61B 5/0022* (2013.01); *A61B 5/0205* (2013.01);
(Continued)

(58) Field of Classification Search
CPC ..... A61B 8/065; A61B 8/0022; A61B 5/0022; A61B 5/0205; A61B 5/0245; A61B 5/113; A61B 5/746; A61B 8/04; A61B 8/06; A61B 8/0833; A61B 8/0883; A61B 8/4236; A61B 8/4281; A61B 8/4427; A61B 8/4455; A61B 8/4472; A61B 8/4477; A61B 8/4494; A61B 8/488; A61B 8/5223; A61B 8/565;
(Continued)

(56) References Cited

U.S. PATENT DOCUMENTS 4,790,322 A 12/1988 Iinuma
5,181,517 A 1/1993 Hickey
(Continued)

FOREIGN PATENT DOCUMENTS

GB 2256710 A 12/1992
JP 2004298249 A 10/2004
(Continued)

*Primary Examiner* — Amanda K Hulbert
*Assistant Examiner* — Natasha Patel
(74) *Attorney, Agent, or Firm* — Chang & Hale, LLP

(57) ABSTRACT

A monitoring system includes a wearable patch device configured to be secured to a body of a patient, the wearable patch device comprising a patch body, a first discrete transducer associated with a first position of the patch body, a second discrete transducer associated with a second portion of the patch body, and a wireless transmitter, and electronics including one or more processors and one or more memory devices and configured to receive signals based on transducer readings of the first and second discrete transducers and determine an amount of blood flow through one or more valves of a heart of the patient based on the signals.

24 Claims, 10 Drawing Sheets

Related U.S. Application Data

(60) Provisional application No. 62/579,709, filed on Oct. 31, 2017.

(51) Int. Cl.

| | | |
|---|---|---|
| *A61B 8/00* | (2006.01) | |
| *A61B 5/0245* | (2006.01) | |
| *A61B 5/0205* | (2006.01) | |
| *A61B 5/00* | (2006.01) | |
| *A61B 8/08* | (2006.01) | |
| *A61B 5/113* | (2006.01) | |
| *A61B 8/04* | (2006.01) | |
| *A61B 5/08* | (2006.01) | |
| *A61B 5/021* | (2006.01) | |
| *A61B 5/022* | (2006.01) | |
| *A61B 7/00* | (2006.01) | |
| *A61B 8/02* | (2006.01) | |

(52) U.S. Cl.
CPC ............ *A61B 5/0245* (2013.01); *A61B 5/113* (2013.01); *A61B 5/746* (2013.01); *A61B 8/04* (2013.01); *A61B 8/06* (2013.01); *A61B 8/0833* (2013.01); *A61B 8/0883* (2013.01); *A61B 8/4236* (2013.01); *A61B 8/4281* (2013.01); *A61B 8/4427* (2013.01); *A61B 8/4455* (2013.01); *A61B 8/4472* (2013.01); *A61B 8/4477* (2013.01); *A61B 8/4494* (2013.01); *A61B 8/488* (2013.01); *A61B 8/5223* (2013.01); *A61B 8/565* (2013.01); *A61B 8/585* (2013.01); *A61B 5/021* (2013.01); *A61B 5/022* (2013.01); *A61B 5/0816* (2013.01); *A61B 7/003* (2013.01); *A61B 8/02* (2013.01); *A61B 8/085* (2013.01); *A61B 8/0841* (2013.01); *A61B 8/4488* (2013.01); *A61B 8/58* (2013.01); *A61B 2505/07* (2013.01); *A61B 2560/0214* (2013.01); *A61B 2560/0223* (2013.01); *A61B 2562/0219* (2013.01)

(58) Field of Classification Search
CPC ......... A61B 8/585; A61B 5/021; A61B 5/022; A61B 5/0816; A61B 7/003; A61B 8/02; A61B 8/0841; A61B 8/085; A61B 8/4488; A61B 8/58; A61B 2505/07; A61B 2560/0214; A61B 2560/0223; A61B 2562/0219; G16H 50/30
USPC ........................................................ 600/301
See application file for complete search history.

(56) References Cited

U.S. PATENT DOCUMENTS

| | | |
|---|---|---|
| 5,551,439 A | 9/1996 | Hickey |
| 5,882,300 A | 3/1999 | Malinouskas et al. |
| 6,544,181 B1 | 4/2003 | Buck et al. |
| 6,682,485 B2 | 1/2004 | Seitz et al. |
| 6,970,742 B2 | 11/2005 | Mann et al. |
| 7,534,209 B2 | 5/2009 | Abend et al. |
| 7,654,960 B2 | 2/2010 | Buck |
| 8,070,684 B2 | 12/2011 | Dala-Krishna |
| 8,750,971 B2 * | 6/2014 | Tran ..................... A61B 5/024 |
| | | 600/509 |
| 8,912,709 B2 | 12/2014 | Pollock et al. |
| 9,033,887 B2 | 5/2015 | Ionasec et al. |
| 2006/0235325 A1 | 10/2006 | Holmstrom et al. |
| 2010/0036253 A1 | 2/2010 | Vezina |
| 2010/0049052 A1 | 2/2010 | Sharf et al. |
| 2010/0076315 A1 | 3/2010 | Erkamp et al. |
| 2011/0184301 A1 | 7/2011 | Holmstrom et al. |
| 2012/0065479 A1 | 3/2012 | Lahiji et al. |
| 2013/0165005 A1 | 6/2013 | Berard-Andersen et al. |
| 2013/0281795 A1 | 10/2013 | Varadan |

FOREIGN PATENT DOCUMENTS

| | | |
|---|---|---|
| WO | 0150962 A1 | 7/2001 |
| WO | 2008101684 A1 | 8/2008 |
| WO | 2017096487 A1 | 6/2017 |

* cited by examiner

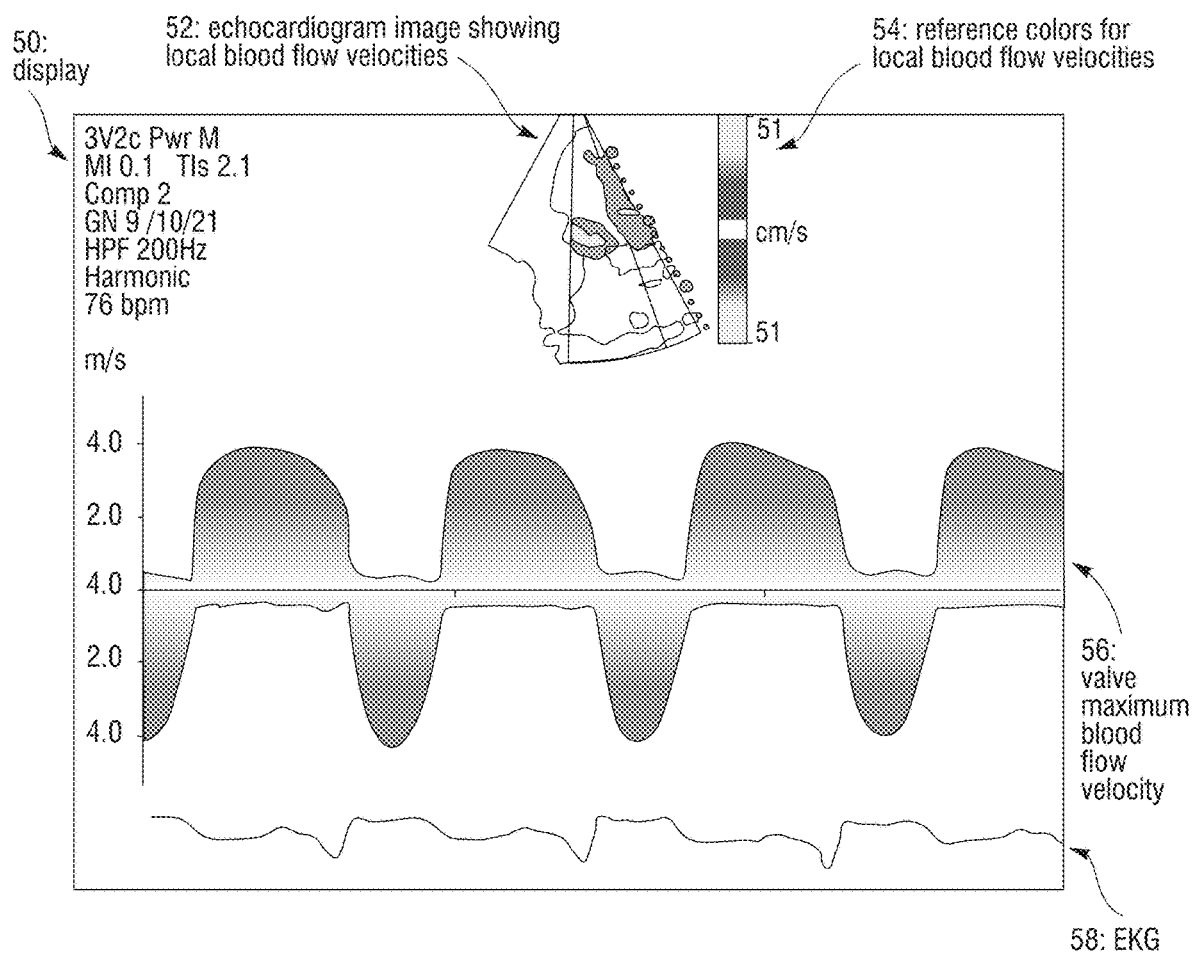

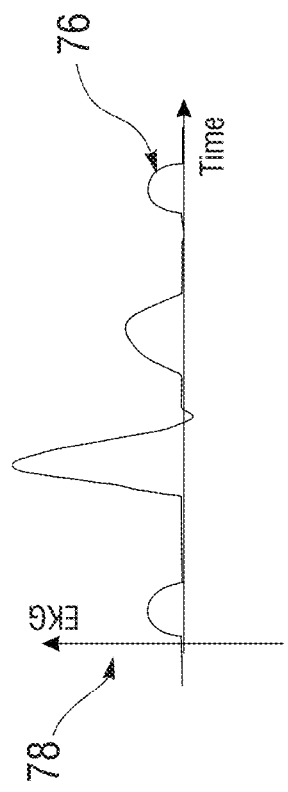
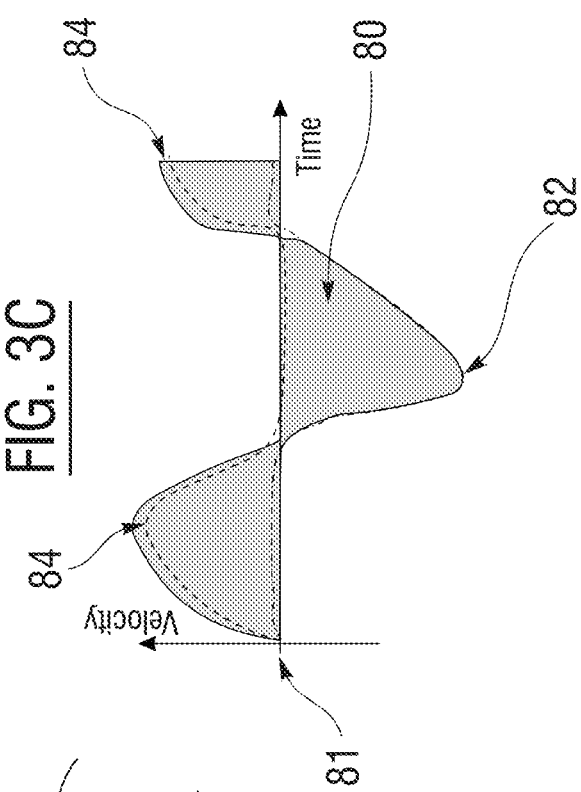
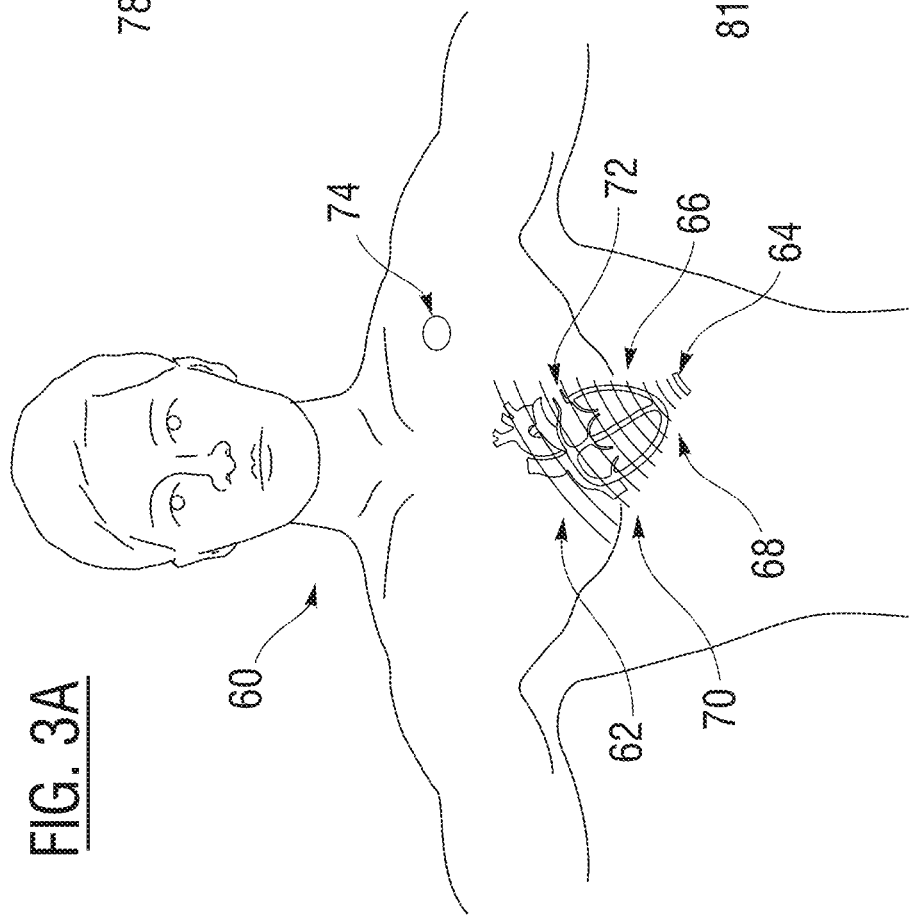

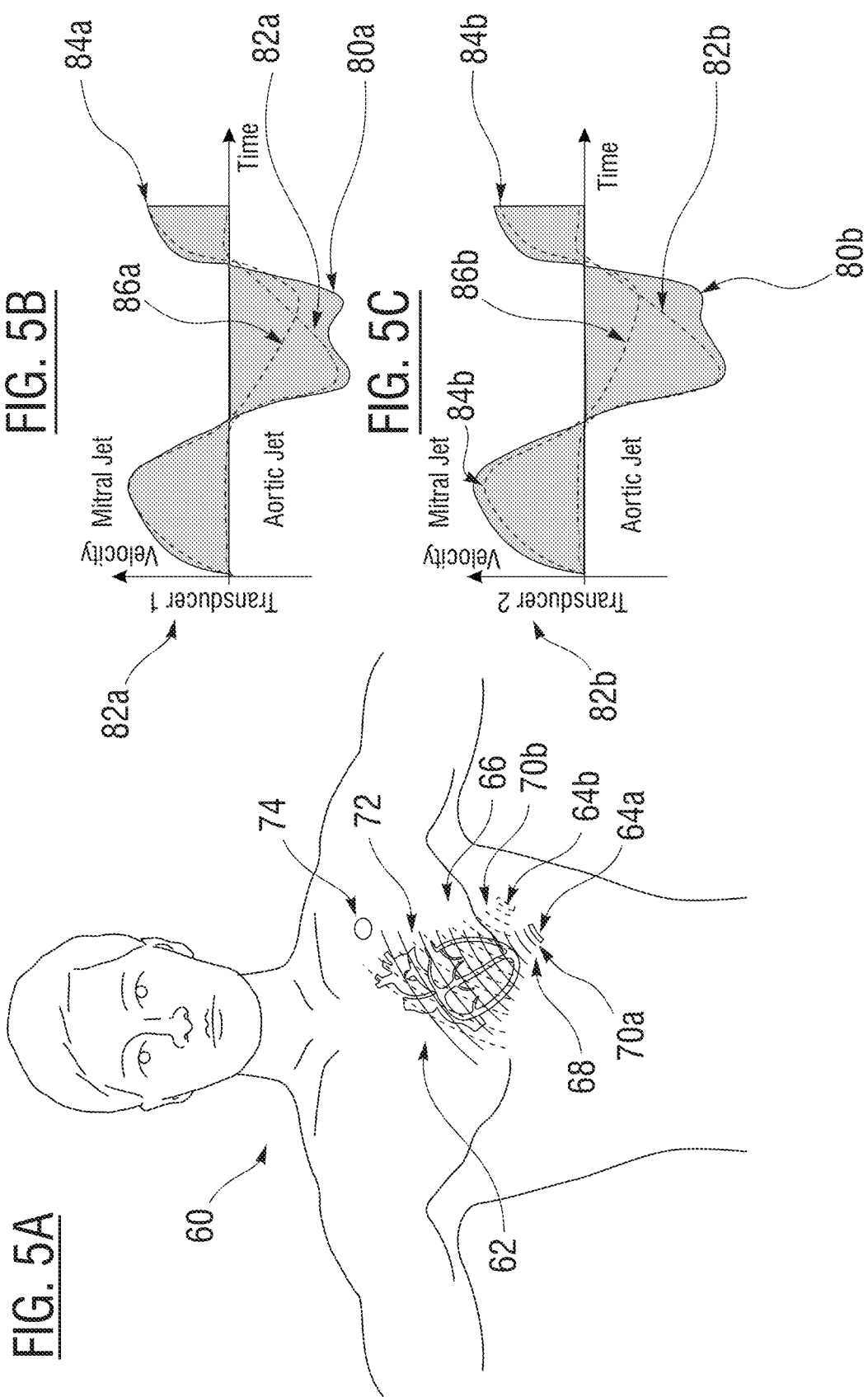

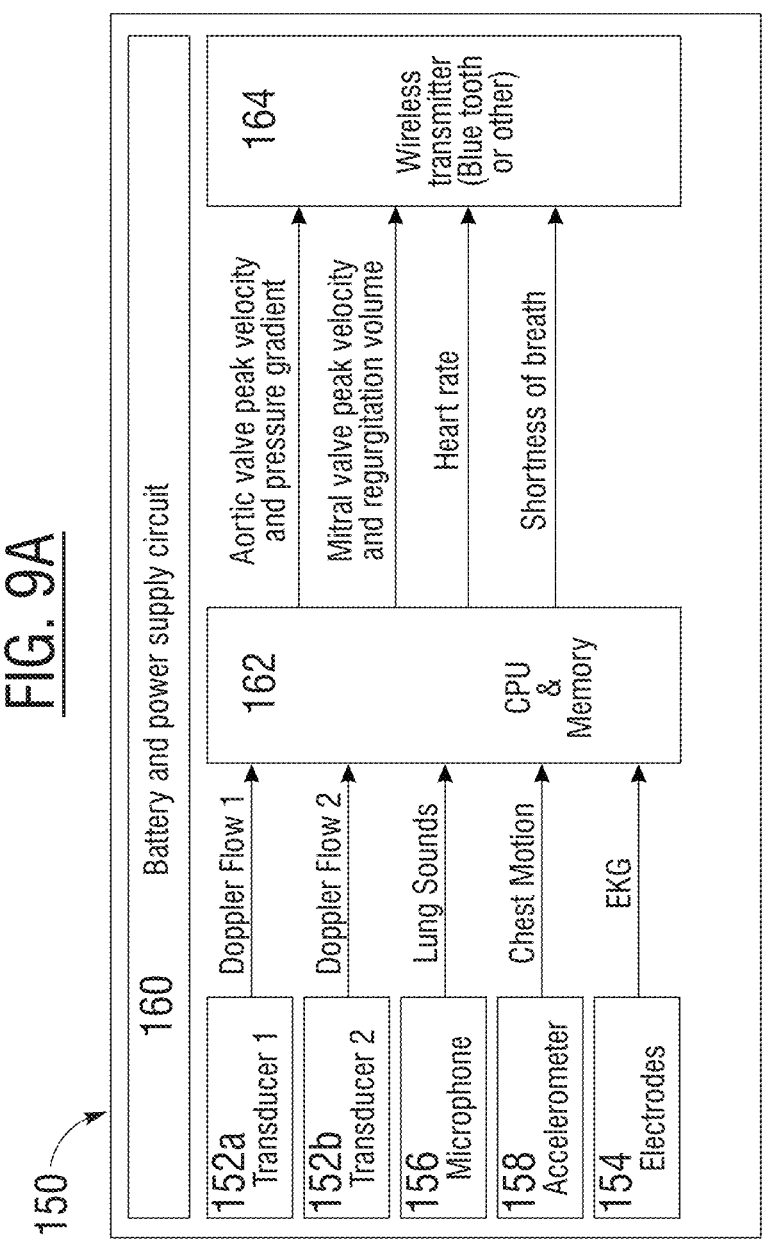
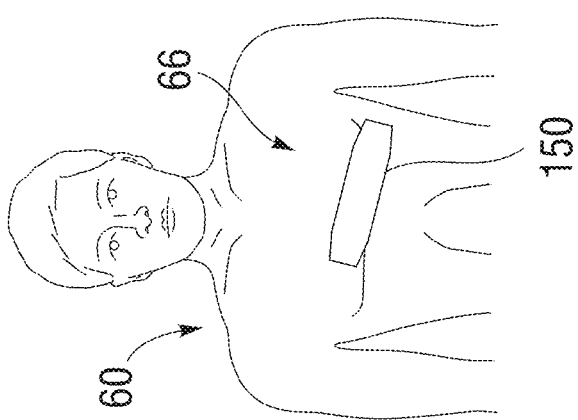
FIG. 9A
FIG. 9B

HEART VALVE MONITORING

CROSS-REFERENCE TO RELATED APPLICATIONS

This application is a continuation of U.S. application Ser. No. 16/171,501, filed on Oct. 26, 2018 and entitled NON-INVASIVE WEARABLE HEART VALVE MONITOR, which claims priority to U.S. Provisional Application No. 62/579,709, filed on Oct. 31, 2017 and entitled NON-INVASIVE WEARABLE HEART VALVE MONITOR, the entire contents of both of which are incorporated herein in their entireties.

FIELD OF THE INVENTION

The present invention relates to monitoring heart function, and, more particularly, to methods and apparatuses for the monitoring of heart valve function by positioning a non-invasive monitoring device on the exterior chest wall.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic, tricuspid, and pulmonary valves usually have three leaflets, while the mitral valve usually has two leaflets.

The operation of the heart, and thus the patient's health, may be seriously impaired if any of the heart valves is not functioning properly. Various problems can develop with heart valves for a number of clinical reasons. Stenosis in heart valves is a condition in which the valves do not open properly. Insufficiency is a condition which a valve does not close properly. Dysfunction of the aortic or mitral valves is most common because they reside in the left side of the heart where pressures and stresses are the greatest.

Heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation. Common examples of such regurgitation include mitral valve regurgitation (i.e., leakage of blood through the mitral valve and back into the left atrium) and aortic valve regurgitation (i.e., leakage through the aortic valve back into the left ventricle). Regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued and short of breath. If left unchecked, the problem can lead to congestive heart failure, arrhythmias, or death.

In many patients who suffer from heart valve regurgitation and other forms of heart disease, careful monitoring of heart parameters is critical to proper patient care. Many technologies are available for invasive-implantable as well as noninvasive wearable monitoring of heart disease patients. These monitors typically use technology to monitor parameters associated with heart failure such as implantable blood pressure sensors, or wearable sensors to monitor EKG, and RF or impedance base sensors to monitor buildup of lung water. For patients with heart valve disease, however, monitoring the disease requires a visit to a clinic or a hospital and an echocardiogram performed by a professional.

To determine the blood flow velocity through the valves, (current) ultrasound systems use echo Doppler. The relative velocity of the blood towards the ultrasound transducer or away from it is detected as a frequency shift of the ultrasonic echo reflected from the blood. Modern ultrasound systems use phased arrays of ultrasound transducers and can differentiate echo signals by the direction from which the signals are coming. The operator can point a cursor to a structure in the ultrasound image (e.g., the center of a specific heart valve) and the phased array will separate the echo coming from that location and analyze blood velocity there. Such phased arrays can provide data that can be processed to create images of the heart and local blood flows, but require trained operator input and assessment and are relatively complex and expensive, and often require relatively high power levels.

What has been needed is a wearable, low-cost, and low-power device for monitoring heart valve function at home. The present invention fulfills this need.

SUMMARY OF THE INVENTION

The present invention provides a number of devices and methods for monitoring valve function. Embodiments of the present invention involve a wearable patch that incorporates one or a small number of discrete transducers to monitor heart valve function continuously at home. The present invention describes a system and method to monitor key parameters of the different valves using simple discrete transducers instead of a phased array, so it could be incorporated in a low-cost low-power disposable adhesive patch. The simple transducers may be simple piezo electric transducers.

A device for monitoring heart valve function according to an embodiment of the invention comprises a patch body, the patch body having a top surface and a bottom surface and a first end and a second end. A pressure sensitive adhesive may be positioned on the bottom surface of the patch body, for securing the device to a patient's chest. Other methods and apparatus for securing the device to the patient's chest are also within the scope of the invention. The device may include a first discrete transducer at a first position on or in the patch body, and may also include a second discrete transducer at a second position on or in the patch body, where the first position and second position may be apart from each other. A power source, such as a battery and/or solar panel, may be provided, as well as a processor configured to receive first transducer data from the first discrete transducer and second transducer data from the second discrete transducer and to calculate blood flows (using well-known echo Doppler calculations) through a first heart valve and/or through a second heart valve.

Various dimensions and configurations of the device are within the scope of the invention. The patch body may have an overall length between 2 cm and 20 cm. The transducers may be positioned 2 cm to 15 cm apart, or 5 cm to 10 cm apart. The first discrete transducer may be positioned at or adjacent the first end of the patch body, and the second discrete transducer may be positioned at or adjacent the second end of the patch body. The power source may comprise a battery configured for inductive recharging. The power source, processor, and/or transducers may be enclosed in a waterproof casing. Each of the discrete transducers may be a discrete piezo-electric transducer.

A device according to the invention may include one or more EKG electrodes, and the processor may be configured to determine heart rate, aortic valve peak velocity, aortic pressure gradient, mitral valve peak velocity, and mitral regurgitation volume using the ultrasonic transducer data and the EKG electrode data. The device may include a microphone and/or an accelerometer, and the processor may be configured to determine shortness of breath using data from the microphone and/or accelerometer. The processor may be configured to calculate left atrial blood pressure, and may include an alarm function that can be triggered by the left atrial blood pressure reaching a designated value.

A system for monitoring heart valve function according to an embodiment of the invention includes a monitor device configured for application to a chest of a patient, with the device having: securing means such as adhesive (e.g., pressure-sensitive adhesive) to secure the device to the chest of the patient; a first discrete transducer; a processor configured to receive first transducer data from the first discrete transducer and to calculate heart valve blood flow using the first transducer data; a power supply; and/or a wireless transmitter. The system may further include a cell phone, wherein the cell phone is configured to receive heart valve blood flow data from the wireless transmitter of the device and also to communicate with a cellular network or an internet connection. The system may include a remote computer, where the remote computer is in communication with the cell phone via the cellular network and/or the internet connection. The remote computer may receive heart valve blood flow data from the cell phone via the cellular network or internet connection, with remote computer located 1 mile or more from the sensor device at a place where the remote computer and the heart valve blood flow data received thereby can be monitored by skilled medical personnel.

In a system of the invention, the device may include one or more EKG electrodes, and/or an accelerometer and/or a microphone. The power supply may comprise a battery and/or a solar panel. The wireless transmitter of the patch may be a Bluetooth transmitter, and the sensor patch may be less than 100 feet from the cell phone. The system may include a blood pressure sensor (such as cuff configured for securement to a patient extremity such as an arm or finger) for determining arterial blood pressure, with the processor configured to calculate left or right atrial blood pressure using the arterial blood pressure and other information such as valve orifice dimensions.

A method for monitoring heart valve function according to an embodiment of the invention includes calibrating ultrasound blood flow signals for one or more transducer positions on the patient's chest; applying a transducer patch to the patient's chest, wherein the transducer patch comprises one or more discrete transducers, wherein applying the transducer patch to the patient's chest comprises positioning at least one of the one or more discrete transducers at each of the one or more transducer positions on the patient's chest; and activating the transducer patch, wherein the transducer patch once activated may be configured to send and receive ultrasonic signals via the at least one discrete transducer, to provide ultrasonic signal data to a processor of the patch, and/or to calculate heart valve blood flow parameters for at least one heart valve using the ultrasonic signal data. The method may include activating a cell phone to receive wireless signals from the transducer patch, wherein the wire wireless signals include heart valve blood flow parameters. The method may include activating a remote computer at a remote distance (such as at least 1 mile) from the transducer patch, wherein the remote computer may be configured to receive heart valve blood flow parameters from the cell phone via a cellular and/or internet connection. The method may include monitoring the received heart valve blood flow parameters via a display of the remote computer.

Applying the transducer patch to the patient's chest may occur after calibrating the ultrasound blood flow signals for the one or more transducer positions. The method may include determining a valve orifice diameter of the patient; storing the valve orifice diameter information in the memory; measuring arterial blood pressure; and repeatedly calculating via the processor the atrial blood pressure using arterial blood pressure, valve gradient, and/or valve orifice area, wherein atrial blood pressure is calculated at least once every day, at least once every hour, or at least once every minute. The valve orifice diameter may be a mitral valve orifice diameter, and the atrial blood pressure may be a left atrial blood pressure.

Applying the transducer patch to the patient's chest may include positioning the first discrete transducer on the patient's chest aimed in a first transducer direction wherein the first transducer direction is closer in alignment to a flow axis of the first valve than to a flow axis of the second valve, may further include positioning the second discrete transducer on the patient's chest aimed in a second transducer direction wherein the second transducer direction is closer in alignment to the flow axis of the second valve than to the flow axis of the first valve. Positioning the patch on the patient's chest may include positioning the patch adjacent or lower than the apex of the patient's heart. Positioning the patch on the patient's chest may include positioning the patch on or adjacent the crease between the pectoral muscle/ breast and the abdominal muscles. The one or more discrete transducers may be two (and only two) discrete transducers, such as piezo-electric transducers.

Other objects, features, and advantages of the present invention will become apparent from a consideration of the following detailed description.

BRIEF DESCRIPTION OF THE DRAWINGS

FIG. 2 depicts a sample of a prior art echocardiogram and echo Doppler output image;

FIG. 3A depicts a front view, in partial cross-section, of a patient with a device according to an embodiment of the invention;

FIGS. 3B-3C depict charts of heart valve performance;

FIG. 5A depicts a front view, in partial cross-section, of a patient with a device according to an embodiment of the invention;

FIGS. 5B-5C depict charts of heart valve performance;

FIG. 9A depicts a block diagram of elements of a device according to an embodiment of the invention;

FIG. 9B depicts a front view of a patient with a device according to an embodiment of the invention.

DETAILED DESCRIPTION OF SEVERAL EMBODIMENTS

Figure 1:
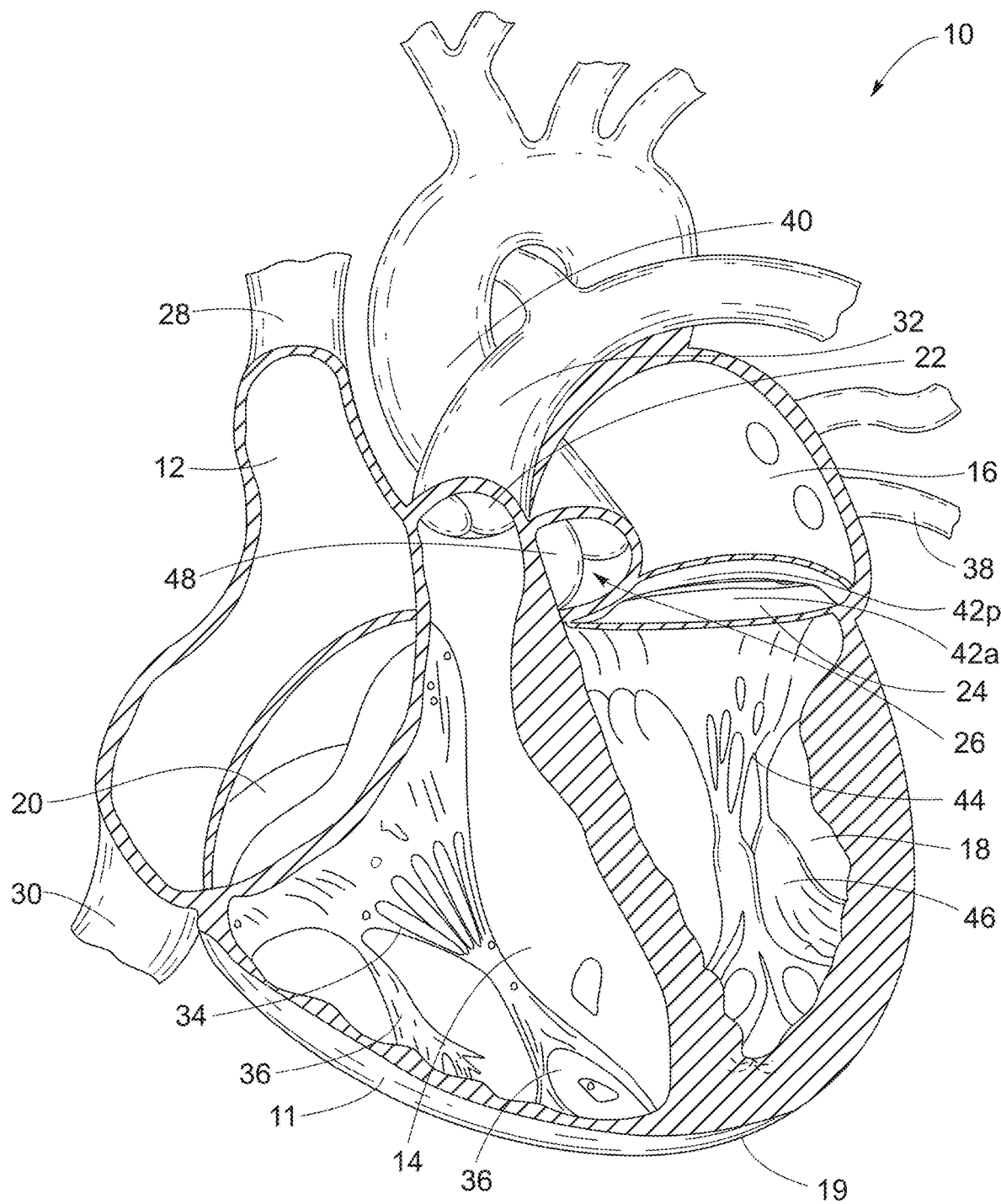
FIG. 1 is a cross-sectional view of a heart.

A cross-sectional view of a human heart 10 is depicted in FIG. 1. The heart 10 has a muscular heart wall 11, an apex 19, and four chambers: right atrium 12; right ventricle 14; left atrium 16; and left ventricle 18. Blood flow is controlled by four main valves: tricuspid valve 20; pulmonary valve 22; mitral valve 24; and aortic valve 26. Blood flows through the superior vena cava 28 and the inferior vena cava 30 into the right atrium 12 of the heart 10. The right atrium 12 pumps blood through the tricuspid valve 20 (in an open configuration) and into the right ventricle 14. The right ventricle 14 then pumps blood out through the pulmonary valve 22 and into the pulmonary artery 32 (which branches into arteries leading to the lungs), with the tricuspid valve 20 closed to prevent blood from flowing from the right ventricle 14 back into the right atrium. Free edges of leaflets of the tricuspid valve 20 are connected via the right ventricular chordae tendinae 34 to the right ventricular papillary muscles 36 in the right ventricle 14 for controlling the movements of the tricuspid valve 20.

After leaving the lungs, the oxygenated blood flows through the pulmonary veins 38 and enters the left atrium 16 of the heart 10. The mitral valve 24 controls blood flow between the left atrium 16 and the left ventricle 18. The mitral valve 24 is closed during ventricular systole when blood is ejected from the left ventricle 18 into the aorta 40. Thereafter, the mitral valve 24 is opened to refill the left ventricle 18 with blood from the left atrium 16. Free edges of leaflets 42a, 42p of the mitral valve 24 are connected via the left ventricular chordae tendinae 44 to the left ventricular papillary muscles 46 in the left ventricle 18 for controlling the mitral valve 30. Blood from the left ventricle 18 is pumped through the aortic valve 26 into the aorta 40, which branches into arteries leading to all parts of the body except the lungs. The aortic valve 26 includes three leaflets 48 which open and close to control the flow of blood into the aorta 40 from the left ventricle 18 of the heart as it beats.

In prior art echocardiogram systems, phased array data can be processed to create images of the heart and local blood flows. An example of a prior art echocardiogram output display 50 is depicted in FIG. 2, including an image 52 of the heart with local blood flows depicted with reference colors 54, a chart of maximum blood flow velocities through the mitral valve 56, and a chart of EKG output 58. While phased arrays used to create such echocardiogram displays can provide detailed information about the heart, they require skilled operator input and assessment and are relatively complex and expensive, as well as requiring relatively high power levels.

A simple transducer device and system according to the invention uses one or a few discrete, non-phased-array ultrasound transducers that collect echo in a beam or beams that target one or more heart valves, and uses signal processing to monitor key parameters of the different valves. It is intended for at-home monitoring of patients suffering from heart valve disease (e.g. aortic stenosis, mitral regurgitation, etc.) for a few days to a few weeks. It can diagnose and document changes in heart valve function during normal life functions (e.g., at work, at home, during exercise, etc.), including changes that were not detected in an ultrasound exam in the hospital or clinic. If such changes are detected by the at-home system of the invention, the system can document the changes, and communicate the changes to a smart phone, which will relay the information back to the physician via a remote computer (such as the physician's smart cell phone or laptop computer or other remote computer device).

A key element of the invention is measuring blood flow velocity in the aortic and mitral valves using echo Doppler via a simple ultrasound transducer or transducers taped on the patient's chest. FIG. 3A depicts a patient 60 with heart 62 monitored by a simple transducer 64 positioned on the patient's chest 66 adjacent the heart apex 68 according to an embodiment of the invention. The transducer 64 produces an ultrasonic beam 70 directed toward one or more heart valves 72. EKG measurements from one or more EKG electrodes 74 on the patient's chest 66 may also be used, and may provide an EKG signal 76 as depicted in the EKG chart 78 of FIG. 3B. Blood flow measurements 80 determined from the Doppler echo from the transducer 64 are depicted in the blood flow chart 81 of FIG. 3C. While all the blood flow within the beam 70 field of view contributes to the Doppler velocity signal and thus the total blood measured blood flow 80, the highest velocities associated with the largest frequency shifts come from the jets through the aortic valve and through the mitral valve. The pressure and flow velocity through the pulmonic and tricuspid valves and flow within the various heart chambers are typically much smaller. In patients with no significant aortic or mitral regurgitation, as depicted in FIG. 3C, the aortic and mitral jets can be separated by their different timing and direction. Peak aortic flow 82 occurs in systole and its direction is negative (away from the transducer on the chest), while peak mitral flow 84 occurs in diastole and its direction is positive (towards the transducer 64 on the chest 66).

Figure 4B:
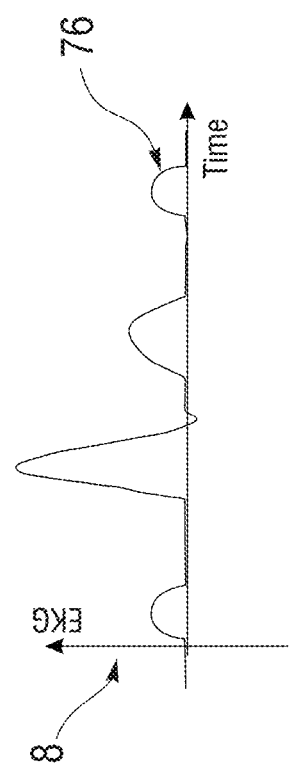
FIGS. 4B-4C depict charts of heart valve performance.
Figure 4C:
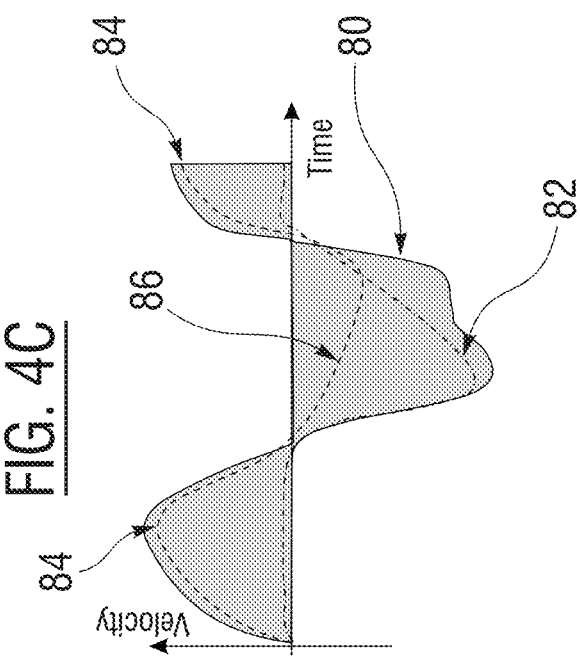
Figure 4A:
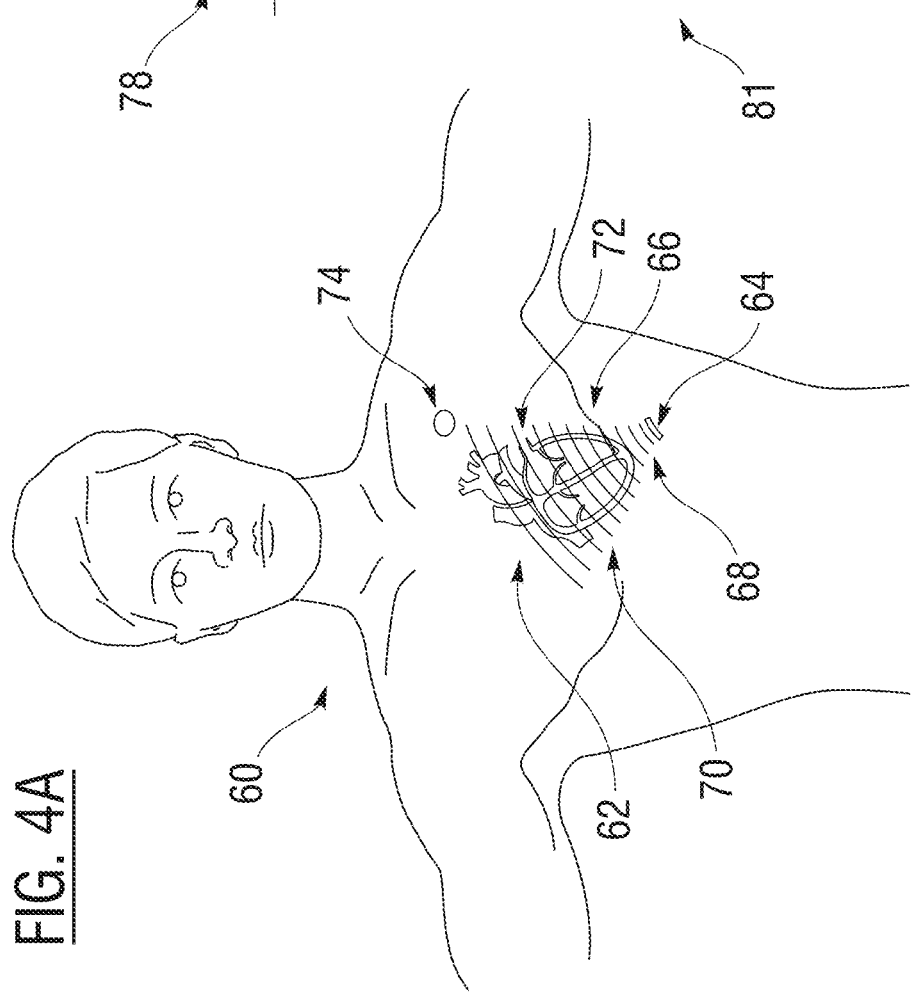
FIG. 4A depicts a front view, in partial cross-section, of a patient with a device according to an embodiment of the invention.

If the patient 60 has significant aortic or mitral valve regurgitation, such as the mitral regurgitation as depicted in FIG. 4C, the regurgitative flow 86 of the mitral valve is away from the transducer at the same time that the proper systolic flow through the aortic valve occurs. More specifically, if the patient has significant mitral regurgitation, the systolic phase is a superposition of forward flow 82 through the aortic valve and regurgitant flow 86 through the mitral valve, both in a direction away from the transducer 62.

For the patient with significant mitral regurgitation, it is important to separate the systolic total flow contribution of the regular flow through the aortic valve from regurgitant flow through the mitral valve in order to properly assess and diagnose the regurgitation. Similarly, for a patient with aortic regurgitation, it is important to separate the diastolic total flow contribution of the regular mitral flow from the regurgitant aortic flow. To simplify the determination of regurgitant flow, the present invention ignores low velocities (such as those within heart chambers or from the tricuspid and pulmonary valves), and assumes that peak velocities have only two contributions: a mitral jet and an aortic jet. To be able to separate the contributions of mitral from aortic, a first transducer 64a is augmented by a second transducer 64b that is added to provide a second independent measurement from a slightly different angle, as illustrated in FIG. 5. Each transducer 64a, 64b provides an ultrasonic beam 70a, 70b, with the beams 70a, 70b at slightly different angles. The respective measured blood flow velocities from each transducer 64a, 64b are depicted in the blood flow charts 82a, 82b.

For every point in time, a set of two equations is solved to isolate the mitral contribution and the aortic contribution. The two transducers 64a, 64b are placed on the chest 66 to differ enough in their angles and distances to the aortic and mitral valves to produce an accurate separation between the two velocities. To add further accuracy or to isolate additional heart valves, more transducers can be added.

Once the two velocity signals (i.e., from the mitral and aortic valves) have been separated, the peak velocity of each signal represents the peak blood velocity through that particular valve, and the area under the curve can be correlated to the total volume flowing. For patients with aortic stenosis, the peak aortic blood velocity is related to the severity of stenosis. For mitral regurgitation patients, the regurgitation volume and flow are related to the severity of mitral regurgitation.

Figure 6:
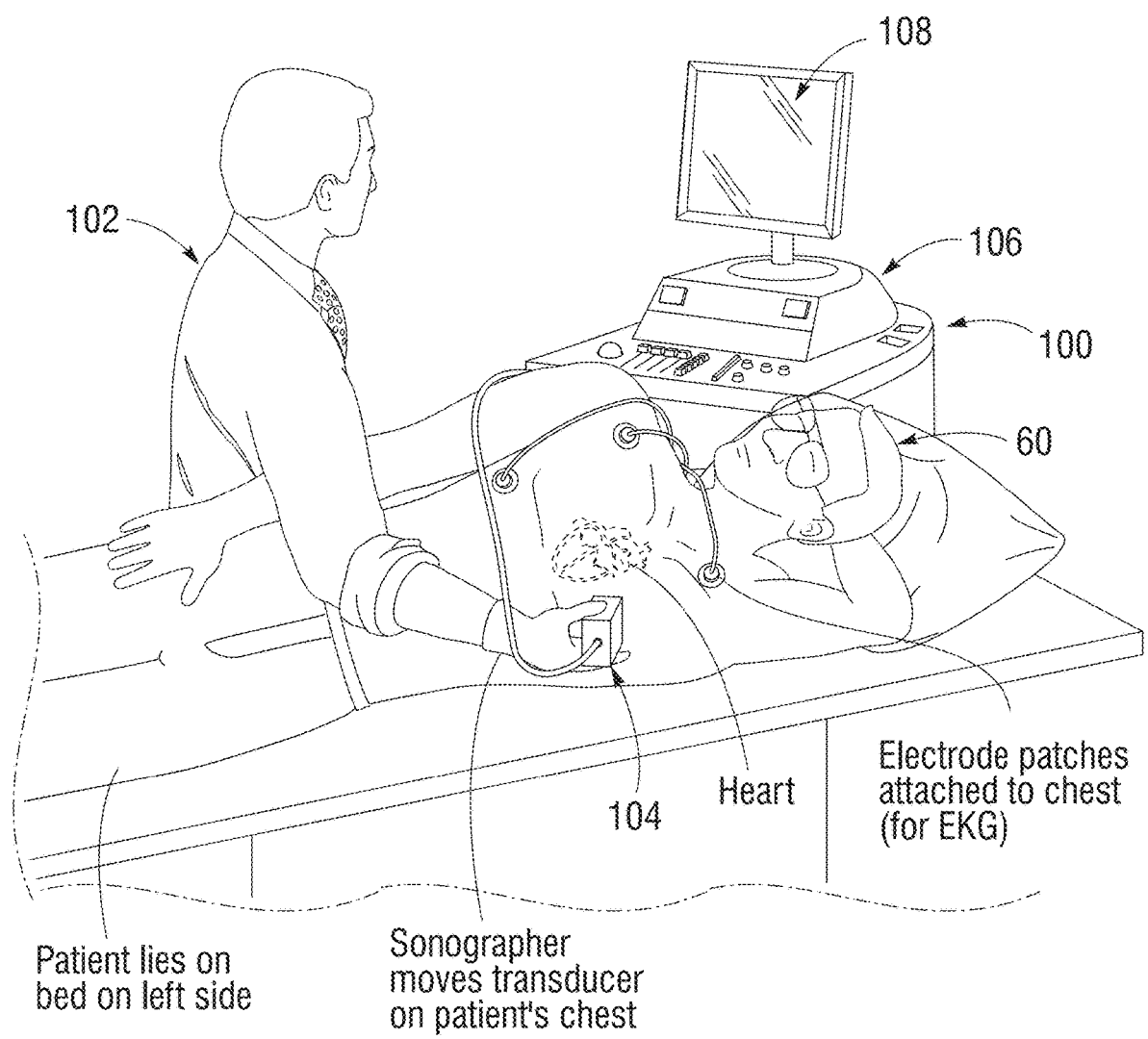
FIG. 6 depicts a perspective view of a patient and doctor calibrating a system according to an embodiment of the invention.

Because one or both of the blood jets (i.e., mitral and aortic) may be at an angle to the transducer(s), and not directly towards or away from the transducer(s), the absolute velocity of the blood jets may need to be calibrated. That can be easily achieved by measuring absolute velocity, one time, in a clinic using a phased array ultrasound system 100 operated by a skilled operator 102 as depicted in FIG. 6. The phased array ultrasound system 100 includes a hand-held phased array transducer 104 providing data to a computer 106 that records and processes the echo Doppler data from the transducer 104 in order to generate an image 108 and/or other data regarding the absolute blood flow velocities. Using the absolute flow data provided by the phased array ultrasound system 100, the skilled operator 102 can thus calibrate the readings from the transducers 64a, 64b of the portable worn device in order to provide accurate blood flow measurements from those transducers. Note that for calibration purposes the skilled operator can position the hand-held phased array transducer in a first position on the patient's chest, take blood flow measurements, then make sure the first transducer 64a is properly secured (e.g., via pressure-sensitive adhesive) to the patient's chest at that first position. Similarly, the skilled operator can position the hand-held phased array transducer in a second position on the patient's chest, take blood flow measurements, then make sure the second transducer 64a is properly secured (e.g., via pressure-sensitive adhesive) to the patient's chest at that second position. The process is repeated for any additional transducers. When the patient 60 goes home, as long as the transducers 64a, 64b do not move relative to the patient's chest 66 the transducers 64a, 64b would remain calibrated for weeks.

The present invention can be used for non-invasive left atrial blood pressure (LABP) measurement at home in heart failure patients that also have mitral regurgitation, which is a large portion of heart failure patients. Heart failure patients often have elevated blood pressure in the left atrium (LABP). Elevated LABP leads to pulmonary congestion, which is the leading cause for hospital admission in heart failure patients. Monitoring LABP has been shown to be a good indicator of the effectiveness of medical therapy and medication, and an upward trend in LABP is a good predictor of pulmonary congestion requiring hospitalization. LABP can be measured in a hospital by inserting a pressure measuring catheter to the left atrium. To monitor LABP at home using prior methods requires an implantable pressure sensor in the left atrium or in the pulmonary artery.

Figure 7:
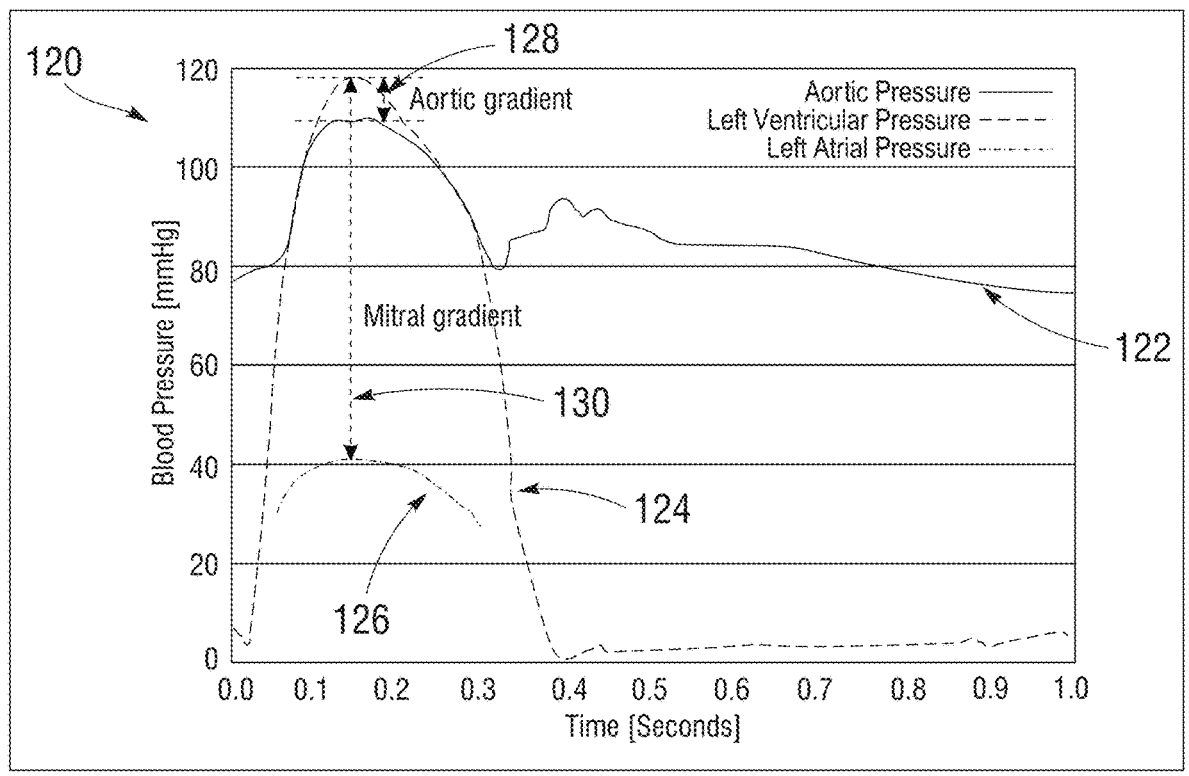
FIG. 7 depicts a chart of heart valve parameters.

In severe mitral regurgitation patients, the peak LABP is actually in systole and not in diastole. The mitral regurgitation through the mitral valve allows the high left ventricular pressure to elevate the left atrial pressure. A way to measure LABP non-invasively is to measure arterial pressure non-invasively using a pressure-cuff on the arm or finger (or even using bio-impedance chest leads), then add the aortic valve gradient as measured by echo to deduce the left ventricular pressure, and then subtract the mitral valve gradient as measured by echo to deduce the left atrial pressure. This method does not provide LABP through the entire cardiac cycle, but it does provide peak pressure because in systole, during and around the peak pressure point, both the aortic valve and the regurgitant mitral valve are open and should allow for simultaneous measurements of pressure gradients. FIG. 7 illustrates a chart 120 showing the relationships of the arterial/aortic pressure 122, the left ventricular pressure 124, and the left atrial pressure 126 to the aortic pressure gradient 128 and the mitral pressure gradient 130 measured by echo at peak systole.

Figure 8:
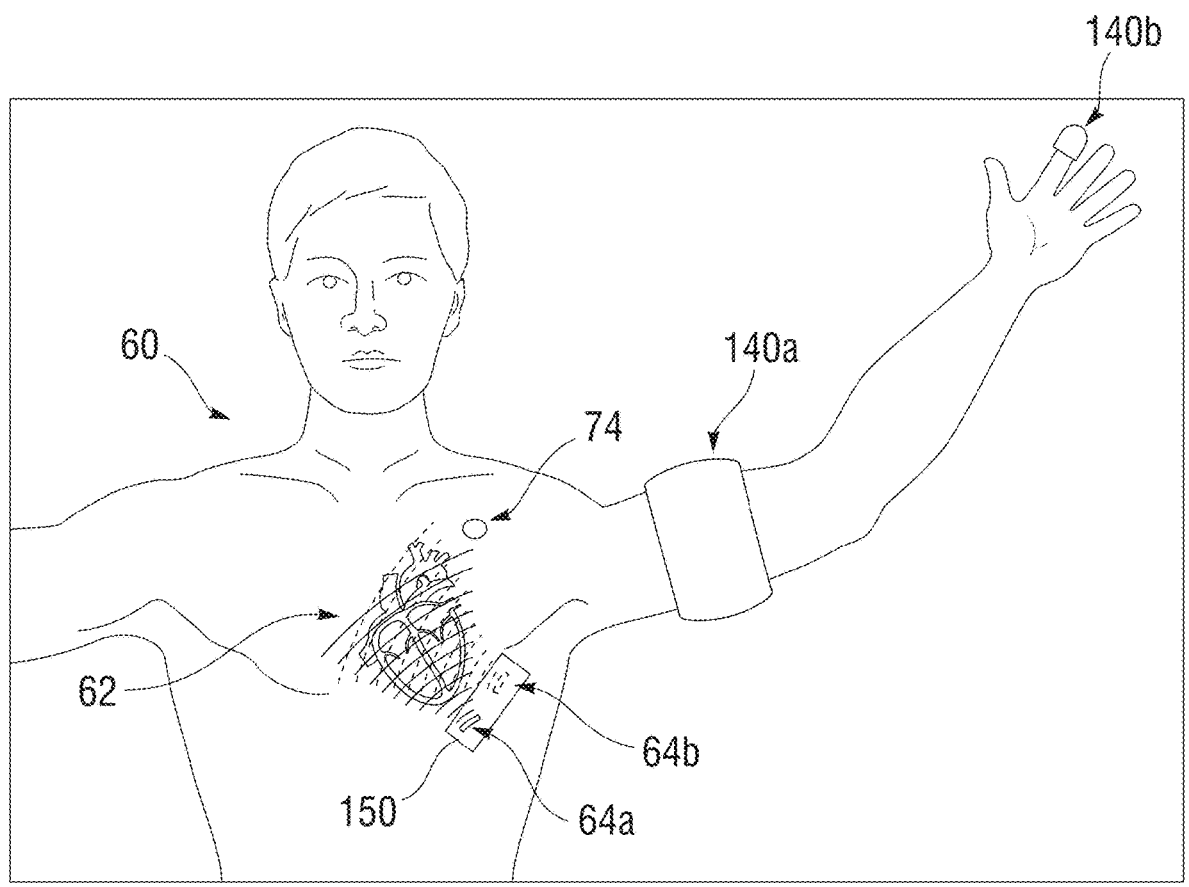
FIG. 8 depicts a front view of a patient with a device according to an embodiment of the invention.
Figure 10A:
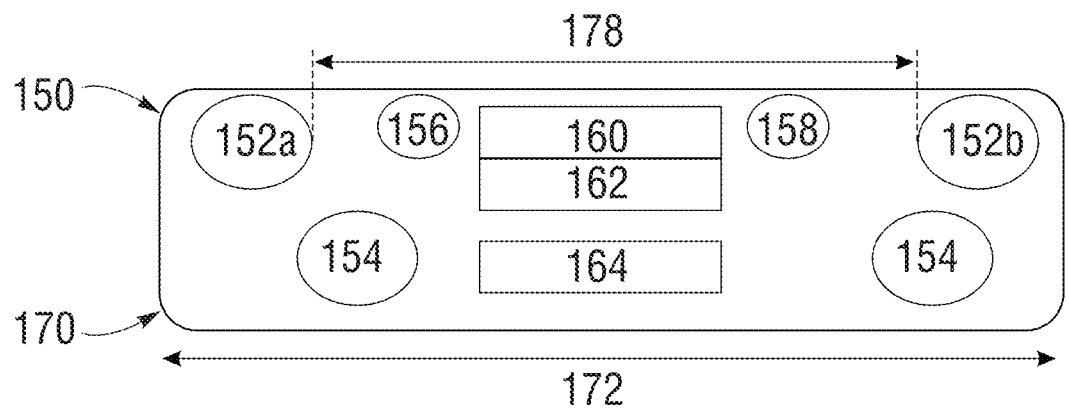
FIGS. 10A-10C depict top, side, and end views, respectively, of a monitoring device according to an embodiment of the invention.
Figure 10B:
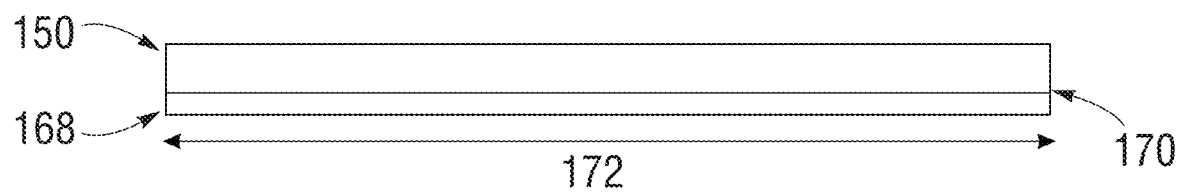
Figure 10C:
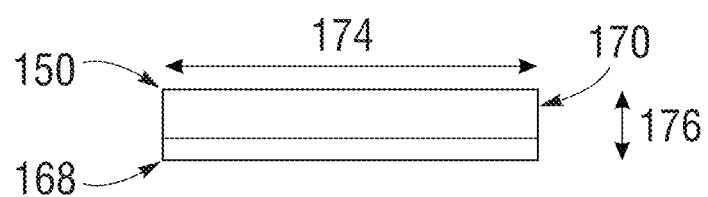

For the system of the present invention to be able to monitor peak LABP at home, components such as transducers, EKG electrodes, CPU processor, etc., may be provided in a wearable patch 150, and two elements are added, as depicted in FIG. 8:

a non-invasive arterial blood pressure measurement, such as via a home cuff 140a, 140b; and a function in the CPU/processor to convert the peak velocities (aortic and mitral) and mitral regurgitation volume to aortic and mitral pressure gradients.

Home cuffs are commonly available for measuring arterial blood pressure, including arm cuffs 140a and finger cuffs 140b as depicted in FIG. 8. The system can also use the EKG electrodes and/or additional electrodes to measure cardio-impedance and convert it to arterial blood pressure continuously. Measurements of blood pressure using cardio-impedance would typically need occasional calibration by an absolute blood pressure measurement with cuff.

Converting the velocity and flow to gradient is relatively complex. To do that conversion, the system requires an estimate of the effective orifice area of the valves involved. The effective orifice area of the aortic valve can be measure and stored during calibration (i.e., by skilled medical personnel in a clinical setting) by echo using the phased array transducers and systems discussed with respect to FIG. 6. Note that the aortic effective orifice area typically does not change quickly with time and can be assumed to be constant for the few weeks of the monitoring period of the system. By contrast, the effective orifice area of the mitral valve changes dramatically with hemodynamic changes of a heart failure patient and cannot thus be assumed to be constant. Echo can measure the orifice area directly and can be used for calibration, although such echo will may require skilled medical personnel using a transducer such as a phased array transducer like that used for calibration of the system such as described with respect to FIG. 6. Instead of a single number such as for the aortic valve, the changing effective orifice area of the mitral valve must be determined as a calibration curve. The system will need multiple calibration points in different hemodynamic conditions (rest vs. stress, or low vs. high heart rate, or low vs. high volume preload) to generate a calibration curve. Once a calibration curve is generated (e.g., in a clinical setting by skilled medical personnel), the home monitor can correlate the mitral regurgitation velocity and volume to a mitral gradient for that specific patient. This makes the calibration session a bit more complex, similar to a stress echo exam instead of a rest-only echo exam, but still less complex than implanting a sensor in a patient's heart.

Note that the system may include one or more alarm functions, such as where alarms are activated if the LABP or other heart function value reaches one or more designated values. For example, an emergency alarm value may be set, where if the calculated LABP or other heart function value reaches the emergency alarm value an emergency alarm is activated in the device, cell phone, and/or remote computer. When activated, the emergency alarm alerts the patient or his/her personal attendants (via the device or cell phone) to proceed to the hospital/emergency room. The emergency alarm may also alert designated medical personnel via the remote computer of the emergency LABP value (or other emergency heart function value) being reached, and may even activate the cell phone to call and/or text and/or email emergency personnel (e.g., paramedics and/or an ambulance) and/or the patient's designated physician/medical personnel to inform them of the emergency value being reached. A cautionary alarm value may be set (in addition to or instead of the emergency alarm value) for the LABP (or other emergency heart function value), which when reached instructs the patient/attendants (via activation of a cautionary alarm on the device and/or cell phone) to make an appointment for the patient to see his or her designated physician in the next day or so, and which may alert designated medical personnel (e.g., via the remote computer) of the cautionary LABP/heart function value being reached. The cautionary alarm may automatically call and/or text and/or email the designated physician/medical personnel with news of the cautionary LABP/heart function value being reached so that the medical personnel can contact the patient to discuss the patient's condition with the patient, schedule follow-up treatment and/or appointments, etc. The cautionary alarm and/or emergency alarm may when activated involve audio signals, such as from a speaker on the device or the cell phone, or other signals such as vibration or visual signals. Note that the emergency and/or cautionary LABP/heart function values may be pre-programmed into the device (and/or cell phone and/or remote computer) based on known emergency values of most patients, although it may be preferred that trained medical personnel program patient-specific emergency and/or cautionary LABP/heart function values into the device. Such patient-specific emergency/cautionary values can be determined by trained medical personnel based on the specific condition of the specific patient, and may be programmed into the device around the time of calibration when the device is applied to the patient's chest.

As depicted in FIGS. 9A-9B and 10A-10C, the two or more transducers can be mounted on an adhesive patch 150 with the necessary electronics 160, 162, 164 and EKG electrodes 154 and attached to a patient as one system. Additional sensors can also be added to the system to diagnose and document more symptoms of valve disease. For example, one important symptom is shortness of breath. To measure shortness of breath a microphone 156 may be added, and/or an accelerometer 158, or both. The microphone 156 can record lung sounds to measure the frequency of breathing. The accelerometer 158 can measure the frequency of breathing by recording chest wall motion. Shortness of breath is characterized by fast shallow breathing. Correlation between shortness of breath and rise in aortic peak velocity is a clear indication of sever aortic stenosis. Correlation between shortness of breath and rise in mitral regurgitate volume is a clear indication of severe mitral regurgitation.

Elements of a patch 150 according to an embodiment of the invention are depicted in FIGS. 9A-9B and 10A-10C. The patch 150 is shaped and sized to be positioned (e.g., via adhesive) on the chest 66 of the patient 60 at a position adjacent the heart apex (not shown), such as being positioned on or adjacent the crease between the pectoral muscle/breast and the abdominal muscles as depicted in FIG. 9B. The patch 150 includes transducers 152a, 152b, and may also include additional sensors such as EKG electrodes 154, microphone 156, and/or accelerometer 158. A power supply 160 is included (e.g., a battery, such as an inductively rechargeable battery, and/or a small solar panel which may be on or in the patch or may be tethered thereto via a power conducting tether line and configured for securement to the patient's clothing), with a CPU and memory 162 configured to use the sensor data to calculate heart parameters such as aortic valve peak velocity and pressure gradient, mitral valve peak velocity and regurgitation volume, heart rate, and/or shortness of breath. Note that for a patient with substantial aortic valve regurgitation, the device may be configured to use the sensor data to calculate heart parameters such as aortic valve peak velocity and regurgitation volume, mitral valve peak velocity and pressure gradient, heart rate, and/or shortness of breath. A wireless transmitter 164 is configured to transmit the calculated heart parameters and/or raw sensor data via wireless (such as Bluetooth) to a cell phone, which can then transmit the calculated heart parameters and/or raw sensor data to a remote location such as computer where skilled medical personnel (e.g., doctors/nurses) can review the parameters/data. The patch 150 may include an adhesive layer 168 (e.g., pressure-sensitive adhesive) on a back side thereof for easy attachment to the patient, and may include a waterproof cover 170 so that the patient can bathe without damaging the patch.

The monitor patch is placed on the patient's chest and calibrated, such as via the procedure described above with respect to FIG. 6. The patient can go home, where any changes or severe episodes of heart valve function are recorded and transmitted to a cell phone and from the cellphone back to the physician in charge.

As depicted in FIGS. 7A-7C, the patch 150 may be configured and dimensioned for easy attachment to the patient with the transducers spaced sufficiently apart for proper measurement of the respective valve flows. The patch 150 may have an overall length 172 of 5 cm to 20 cm, 8 to 17 cm, or 10 to 15 cm; an overall width 174 of 2 cm to 5 cm, 3 cm to 4 cm, or 5 cm or less; and/or an overall thickness 176 of 1 cm or less, 0.5 cm or less, or 0.25 cm or less. Note that other dimensions are within the scope of the invention. The transducers 152a, 152b may be spaced apart a distance 178 of 2 cm to 15 cm, or 5 cm to 10 cm, to provide appropriate spacing between the transducer signals in order to separate the measured blood flows of the aortic and mitral valves. The patch 150 may be flexible to better conform to the surface of the patient's chest. Note that transducers for use with the invention may have diameters (if circular)/maximum dimension (if non-circular) of 3 cm or less, 2 cm or less, 1 cm or less.

The monitor patch 150 may be low cost and therefore disposable. After a few weeks, when the battery 160 is empty, the patch 150 may be taken off and disposed of. For patients requiring longer term monitoring, the patient may be able to self-apply a new patch when the old one is discarded, as long as care is taken to make sure that the transducers of the new patch are positioned at the same positions as the transducers of the old patch.

Note that the system may include multiple patches, such as a first patch having the transducers, a second patch having EKG electrodes, a third patch having the microphone or accelerometer, etc. The multiple patches may each have a dedicated battery and/or transmitter and/or processor/memory and may be linked via wireless transmissions, and/or may be linked via wires and may share power and/or transmitters and/or processors/memory.

Although the specific embodiments discussed above are directed toward mitral and aortic valve monitoring, the invention may also be applicable for use in monitoring other heart valves, including the tricuspid and pulmonary valves.

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

Although methods and materials similar or equivalent to those described herein can be used in the practice or testing of the present disclosure, suitable methods and materials are described above. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A monitoring system comprising:
   a wearable patch device configured to be secured to a body of a patient, the wearable patch device comprising a patch body, a first discrete transducer associated with a first position of the patch body, a second discrete transducer associated with a second portion of the patch body, and a wireless transmitter; and
   electronics including one or more processors and one or more memory devices and configured to:
   receive signals based on transducer readings of the first and second discrete transducers; and
   determine an amount of blood flow through one or more valves of a heart of the patient based on the signals.

2. The system of claim 1, wherein the electronics are part of a smart phone communicatively coupled to the wearable patch device.

3. The system of claim 1, wherein the electronics are part of a remote computing system coupled to the wearable patch device over one or more communication networks.

4. The system of claim 1, wherein the electronics are further configured to determine a first component of the amount of blood flow attributable to regular flow through a first heart valve, and a second component of the amount of blood flow attributable to regurgitant flow through a second heart valve.

5. The system of claim 4, wherein the electronics are further configured to determine a total flow volume through the first heart valve based at least in part on the first component of the amount of blood flow.

6. The system of claim 5, wherein the total flow volume is determined using pre-determined absolute flow calibration data.

7. The system of claim 6, wherein the absolute flow calibration data is based on absolute flow data provided by a phased array ultrasound system.

8. The system of claim 6, wherein the absolute flow calibration data correlates absolute flow values with measured flow values based on data from the first and second discrete transducers.

9. The system of claim 1, wherein the first discrete transducer is oriented at a different angle than the second discrete transducer.

10. A monitoring device comprising:
    a patch body configured to be secured to a chest of a patient at a position adjacent to an apex of a heart of the patient;
    a first transducer associated with a first portion of the patch body;
    a second transducer associated with a second portion of the patch body;
    power supply circuitry in electrical communication with the first and second transducers and configured to provide power thereto; and
    control circuitry configured to receive transducer signals from the first and second transducers and wirelesly transmit signals that are indicative of blood flow velocity through a valve of the heart based at least in part on the transducer signals.

11. The monitoring device of claim 10, wherein the first transducer and the second transducer are ultrasound transducers configured to transmit ultrasound signals through tissue of the patient and receive reflected ultrasound signals.

12. The monitoring device of claim 10, wherein the first transducer is oriented at a different angle than the second transducer.

13. The monitoring device of claim 10, further comprising one or more electrocardiogram electrodes.

14. The monitoring device of claim 10, further comprising an accelerometer configured to generate signals indicative of a frequency of breathing of the patient.

15. The monitoring device of claim 10, further comprising an adhesive layer configured to secure the patch body to the chest of the patient.

16. The monitoring device of claim 10, further comprising a microphone configured to detect audio signals indicative of breathing of the patient.

17. The monitoring device of claim 10, wherein the power supply circuitry is coupled to a wearable solar panel.

18. The monitoring device of claim 10, wherein the first portion of the patch body is separated from the second portion of the patch body by a distance of between 2 cm and 15 cm.

19. A method for monitoring heart valve function, the method comprising:
   securing a patch device on a chest of a patient, the patch device comprising a first ultrasound transducer associated with a first portion of the patch device, a second ultrasound transducer associated with a second portion of the patch device, and a wireless transmitter;
   transmitting first and second ultrasound signals into the patient's chest using the first and second ultrasound transducers, respectively;
   receiving first and second reflected signals from the first and second ultrasound signals, respectively; and
   determining an amount of blood flow through one or more valves of a heart of the patient based at least in part on the first and second reflected signals.

20. The method of claim 19, wherein the first ultrasound transducer is oriented at a different angle than the second ultrasound transducer.

21. The method of claim 19, further comprising:
   positioning a handheld phased array transducer in a first position on the patient's chest;
   taking blood flow measurements using the handheld phased array transducer at the first position;
   securing the first ultrasound transducer on the patient at the first position;
   positioning the handheld phased array transducer in a second position on the patient's chest;
   taking blood flow measurements using the handheld phased array transducer at the second position; and
   securing the second ultrasound transducer on the patient at the second position.

22. The method of claim 19, further comprising using a pressure cuff to measure arterial pressure of the patient using the pressure cuff, and determining left atrial pressure based at least in part on the first and second ultrasound signals and the measured arterial pressure.

23. The method of claim 22, further comprising determine peak flow velocity through the one or more valves of the heart of the patient based at least in part on the first and second reflected signals, and determining one or more heart valve pressure gradients based on the peak flow velocity, wherein said determining the left atrial pressure is based in part on the one or more heart valve pressure gradients.

24. The method of claim 23, wherein said determining the one or more heart valve pressure gradients is based on an effective orifice area of at least one of the one or more valves.

* * * * *